US005463127A

United States Patent [19]
Deavenport et al.

[11] Patent Number: 5,463,127
[45] Date of Patent: Oct. 31, 1995

[54] PROCESS FOR PREPARATION OF HALOHYDROXYPROPYL-TRIALKYL-AMMONIUM HALIDES

[75] Inventors: Joseph L. Deavenport, Richwood; Bladimir I. Lopez, Sweeny, both of Tex.

[73] Assignee: The Dow Chemical Company, Midland, Mich.

[21] Appl. No.: 373,141

[22] Filed: Jan. 17, 1995

[51] Int. Cl.$^6$ .................................................. C07C 209/02
[52] U.S. Cl. .................................................. 564/292; 564/296
[58] Field of Search .................................................. 564/281, 292, 564/296

[56] References Cited

U.S. PATENT DOCUMENTS

| | | | |
|---|---|---|---|
| 2,876,217 | 3/1959 | Paschall | 260/531 |
| 3,135,788 | 6/1964 | Noguchi et al. | 260/531 |
| 3,649,616 | 3/1972 | Goldstein et al. | 260/233.3 |
| 3,718,639 | 2/1973 | Falkehag et al. | 260/124 A |
| 4,066,673 | 1/1978 | Doughty et al. | 260/348.13 |
| 4,216,156 | 8/1980 | Smid | 260/348.38 |
| 4,359,006 | 10/1982 | Bankert | 525/239.5 |
| 4,421,932 | 12/1983 | Rutzen et al. | 564/292 |
| 4,450,295 | 5/1984 | van der Mass | 564/294 |
| 4,594,452 | 6/1986 | Reimschuessel et al. | 564/292 |
| 4,602,110 | 7/1986 | Tasset | 564/292 |
| 4,645,794 | 2/1987 | Davis et al. | 525/61 |
| 4,690,817 | 9/1987 | Davis et al. | 424/70 |
| 4,814,506 | 3/1989 | Katayama et al. | 564/292 |
| 5,077,435 | 12/1991 | Kimbrell | 564/292 |
| 5,112,886 | 5/1992 | Phalangas | 523/332 |
| 5,196,582 | 3/1993 | Smith et al. | 564/292 |

FOREIGN PATENT DOCUMENTS

| | | |
|---|---|---|
| 005223A2 | 11/1979 | European Pat. Off. . |
| 58-174349 | 10/1983 | Japan . |
| 61-106544A | 5/1986 | Japan . |
| 61-130281A | 6/1986 | Japan . |
| 2-295952 | 12/1990 | Japan . |
| 63-287587A | 12/1991 | Japan . |
| 4-145054 | 5/1992 | Japan . |
| 2092150 | 8/1992 | United Kingdom . |

OTHER PUBLICATIONS

Yu, Shuming et al., "Manufacture of 3–chloro–2–hydroxypropyltri–methylammonium chloride", (Huaxue Shijie 1989, 30(1), 11–13), (Chemical Abstract 111:59824k) Translation.
Chemical Abstract 98:53161h, (Aug. 6, 1982), (FR 2,499, 080).
Chemical Abstract 83:27637p, (Feb. 21, 1975), (JP 75–05, 323).
Chemical Abstract 83:113651v, (Feb. 15, 1975), (JP 75–14, 628).
Chemical Abstract 85:5477a, (May 29, 1975), (JP 75–62, 917).
Chemical Abstract 90:151565x, (Nov. 14, 1978), (JP–78–130, 610).
Chemical Abstract 106:50010f, (Jun. 21, 1986), (JP 61–134, 383).
Chemical Abstract 121:83033, (Apr. 26, 1994), (JP 06–116, 255 A2).
Chemical Abstract 121:108495, (May 24, 1994), (JP 06–145,156 A2).
Chemical Abstract 58:7830b, (May 11, 1962), (JP 62–001, 708).
Chemical Abstract 59:1754b, (Jun. 19, 1962), (JP 62–005, 171).
Chemical Abstract 96:34528a, (Jul. 15, 1981), (CS 188, 733).
Chemical Abstract 87:86710n, (Apr. 4, 1977), (JP 77–042, 811).
Chemical Abstract 114:96814q, (Sep. 13, 1990), (JP 02–231, 402).
Chemical Abstract 80:26707n (Yakugaku Zasshi 1973, 93(10), 1342–8).
Chemical Abstract 106:4519f, (May 22, 1986), (JP 61–020, 535).
Chemical Abstract 94:15540r, (Jul. 5, 1980), (JP 80–089, 273).
Chemical Abstract 103:16099n, (May 5, 1985), (JP 60–096, 678).
Derwent Abstract 87–302846, (Sep. 18, 1987), (JP 62–212, 352).
Derwent Abstract 86303X, (Oct. 15, 1976), (NL 151,081).
Derwent Abstract 60272P, (Oct. 29, 1965), (BE 671,687).
Derwent Abstract 25156X, (Feb. 17, 1976), (JP 51–019, 710).
Derwent Abstract 28811B, (Mar. 6, 1979), (JP 54–030,109).
Derwent Abstract 86–173339, (May 25, 1986), (JP 61–106, 544–A), Translation.
Derwent Abstract 86–199700, (Jun. 18, 1986), (JP 61–130, 281–A) Chemical Abstract 106:67083e, (Jun. 18, 1986), (JP 61–130,281–A) Translation.
Derwent Abstract, (Dec. 18, 1991), (JP 03–287,567–A) Chemical Abstract 116:213992a, (Dec. 18, 1991), (JP 03–287,567–A) Translation.

*Primary Examiner*—Gary E. Hollinden
*Assistant Examiner*—Brian M. Burn

[57] ABSTRACT

The present invention is a process for producing halohydroxypropyltrialkylammonium halides by reacting, in a reaction mixture, a trialkylamine hydrohalide and the corresponding free amine with an epihalohydrin, wherein the free trialkylamine is present in an amount corresponding to from about 1 to about 10 mole percent of the combination of free amine and amine hydrohalide and wherein the epihalohydrin is admixed and allowed to react for a first period of time with the free amine and hydrohalide salt at a first temperature less than a second temperature at which the epihalohydrin is allowed to further react with the amine and hydrohalide salt for a second period of time wherein the second temperature is sufficiently greater than the first that less unreacted amine is present after reaction than is present if the same reactants are admixed and reacted at the first temperature for a time equal to the sum of the first and second periods of time. The epichlorohydrin is preferably admixed and allowed to react with the free amine and amine hydrohalide at a first temperature of from about 0° C. to about 15° C. for the first period of time and the admixture is allowed to react further at a second temperature less than 50° C. but at least 15° C. for the second period of time. More preferably, the first period includes an addition period and a digest period.

10 Claims, No Drawings

PROCESS FOR PREPARATION OF HALOHYDROXYPROPYL-TRIALKYL-AMMONIUM HALIDES

This invention relates to the preparation of halohydroxypropyltrialkylammonium halides.

Halohydroxypropyltrialkylammonium halides are known to be useful as intermediates used in modification of natural and synthetic polymers, particularly in production of cationic polysaccharides, e.g. starch.

Halohydroxypropyltrialkylammonium halides are generally prepared by reaction of certain trialkylamines or their salts with epihalohydrins for instance by methods taught in European Patent Application No. 55,796 and U.S. Pat. Nos. 2,876,217; 3,135,788; 4,450,295 and 4,594,452. U.S. Pat. No. 2,876,217 discloses reactions of epihalohydrins and certain tertiary amines or salts in aqueous systems at a pH of at least 5. Use of such a method results in a series of by-products, including unreacted epihalohydrins and 1,3-dihalo- 2-propanol, which are preferably removed by careful purification by solvent extraction or vacuum distillation. European Patent Application No. 55,796 and U.S. Pat. No. 3,135,788 also disclose aqueous systems for similar reactions which require careful purification.

In the prior art the salts of trialkylamines are typically used rather than the free amines to avoid production of epoxypropyl (glycidyl) compounds rather than the desired halohydroxypropyl compounds. However, Japanese Kokai 04-145054 (1992) discloses a synthesis using trialkylamine and a hydrogen halide in less than a stoichiometric amount; the acid is used in an amount corresponding to 10–95 mole percent of the amine to achieve partial neutralization. A temperature of from −10° C. to 50° C. is used. This reference explains the problems with by-product production in the prior art using completely neutralized amine. It also reveals production of by-product diquaternary and diol product and epoxide along with a high residual amine concentration after the synthesis.

It would be desirable to have a process for making halohydroxypropyltrialkylammonium halides which produces a high yield of the desired product and less by-products especially diquaternary compounds, or less residual trialkylamine (which is commonly in the hydrochloride form after reaction) than is observed with prior art processes.

SUMMARY OF THE INVENTION

In one aspect the invention is a method for producing a halohydroxypropyltrialkylammonium salt by reacting, in an aqueous reaction mixture, a trialkylamine salt and the corresponding free amine with an epihalohydrin, wherein the free trialkylamine is from about 1 to about 10 mole percent of the combined trialkylamine hydrochloride and free amine and wherein the epihalohydrin is admixed and allowed to react for a first period of time with the free amine and hydrohalide salt at a first temperature less than a second temperature at which the epihalohydrin is allowed to further react with the amine and hydrohalide salt for a second period of time wherein the second temperature is sufficiently greater than the first that less unreacted amine is present after reaction than is present if the same reactants are admixed and reacted at the first temperature for a time equal to the sum of the first and second periods of time. The epichlorohydrin is preferably admixed and allowed to react with the free amine and amine hydrohalide at a first temperature of from about 0° C. to about 15° C. and the resulting admixture is allowed to react further at a second temperature less than 50° C. but at least 15 ° C.

This process advantageously produces high yields of desired product with low yields of by-products, especially diquaternary compound, and low levels of starting trialkylamine remain in the final solution. Advantageously, product purification is facilitated and environmental concern alleviated by having a lower amount of organic by-product produced.

DETAILED DESCRIPTION OF THE INVENTION

The process of the invention is widely applicable and is particularly useful for preparation of 3-chloro-2-hydroxypropyltrimethylammonium chloride from trimethylamine and trimethylamine hydrochloride reacted with epichlorohydrin. While the description is partially given in terms of that specific example for clarity, the invention is not so limited.

The process of the invention is suitable for any trialkylamine and the corresponding hydrohalide but is particularly useful for trialkylamines and their hydrohalides such as trimethylamine, tri-n-propylamine, dimethyl stearylamine, dimethyl dodecylamine, triethylamine, tri-n-butylamine, tri-n-hexylamine, dimethylmonoethylamine, dimethylmono-n-butylamine, dimethylcyclohexylamine, dimethyl-monoisopropylamine, methylethyl-n-propylamine, methylethyl-n-butylamine, methyl dialkyl amines, and other tertiary amines having linear, branched, or cyclic hydrocarbon groups each independently containing from 1 to 20 carbon atoms, and their hydrohalide preferably dimethylstearylamine, dimethyl dodecylamine or trimethylamine, and their hydrohalides more preferably trimethylamine and its hydrohalides, particularly its hydrochloride.

The trialkylamines and their salts are commercially available, or are formed in reactions within the skill in the art such as the reaction of the corresponding trialkylamine with an acid, preferably a hydrohalic acid, to form the amine hydrohalide, more preferably with hydrochloric acid. While the hydrohalide is preferred, any acid would sufficiently neutralize the base to be useful in the practice of the invention; therefore, any acid salt is suitable in the present invention, preferably salts which do not form a buffer, more preferably inorganic acid salts, most preferably monovalent inorganic salts such as nitrates or divalent inorganic salts such as sulfates, but also organic salts such as the acetate, or formate.

Any epihalohydrin is suitably used, but epichlorohydrin is the preferred epihalohydrin because it is readily available and chloride ion is considered more environmentally acceptable than other halides.

In a preferred embodiment, trialkylamine is admixed with the corresponding trialkylammonium salt, preferably hydrohalide, preferably in aqueous solution, most preferably both the amine and hydrohalide are in aqueous solution. While any concentration of the amine combined with trialkyl amine salt are suitable for use in the practice of the invention, for convenience and to achieve a desirable rate of reaction with epihalohydrin while avoiding excessive waste water handling, the initial concentrations are preferably sufficiently high to achieve a rapid rate of reaction, conveniently at least about 10 weight percent, but insufficient to precipitate the salt or product, thus less than about 60 weight percent more preferably from about 40 to about 60, most preferably from about 55 to about 60 weight percent based on the combined amine and hydrohalide weight based on aqueous admixture before the epihalohydrin addition. Alternatively, an amine is partially neutralized with the acid, preferably hydrohalic acid or an amine salt is partially neutralized with a base. Partial neutralization optionally takes place in situ, e.g. by simultaneous or sequential addition of amine and acid. Any means within the skill in the art for forming admixtures of the free amine and its salt in the preferred ratios is suitable for use in the practice of the invention.

The amine and hydrohalide are conveniently admixed just prior to reaction with epihalohydrin. Alternatively, an admixture is prepared in advance or obtained commercially. If the admixture is stored, it is advantageous to store the mixture in a closed container to prevent free amine from escaping when the amine is volatile.

Sufficient amine is admixed with or otherwise present with the amine salt, preferably hydrohalide, to reach an initial pH (before addition of epihalohydrin) of from about 8.1 to about 9.2, preferably from 8.1 to about 9.0, more preferably from about 8.1 to about 8.9 at 10° C. These pH's correspond to an amine hydrohalide to total free amine plus amine hydrohalide percentage of from about 99.0 to about 90.0, preferably from 99.0 to about 93.0 more preferably from about 99.0 to about 95.0 as calculated based on a chart of pKa's of trimethylamine and corresponding temperatures from *Dissociation Constants of Organic Bases in Aqueous Solution* by D. D. Perrin (Butterworths, London, 1965, p 15) reproduced below. This percentage corresponds to the mole percentage of hydrohalic acid used to neutralize amine.

| pKa of Trimethylamine | Temperature (°C.) |
| --- | --- |
| 10.355 | 0 |
| 10.128 | 10 |
| 9.907 | 20 |
| 9.692 | 30 |
| 9.477 | 40 |
| 9.270 | 50 |

As the table shows, measured pH varies with temperature. For instance, a pH of 8.5 measured at 30° C. corresponds to 94 mole percent trimethylamine hydrochloride, but the same pH measured at 20° C. corresponds to 96.4 mole percent trimethylamine hydrochloride. The present invention is, therefore, defined in terms of mole percent hydrohalide salt based on combined free amine and hydrohalide salt, and the pH is stated for convenience as that measured at 10° C. For convenience, the following chart gives corresponding mole percentage trimethylamine (TMA) and pH calculated at 15° C. and molar concentration:

| mole % TMA | mole % TMA—HCl | [$H_3O^+$] | pH |
| --- | --- | --- | --- |
| 0.1 | 99.9 | 9.5E-08 | 7.02 |
| 0.2 | 99.8 | 4.75E-08 | 7.32 |
| 0.5 | 99.5 | 1.89E-08 | 7.72 |
| 0.7 | 99.3 | 1.35E-08 | 7.87 |
| 0.8 | 99.2 | 1.18E-08 | 7.93 |
| 1 | 99 | 9.41E-09 | 8.03 |
| 1.5 | 98.5 | 6.24E-09 | 8.20 |
| 1.8 | 98.2 | 5.19E-09 | 8.28 |
| 2 | 98 | 4.66E-09 | 8.33 |
| 2.3 | 97.7 | 4.04E-09 | 8.39 |
| 3 | 97 | 3.07E-09 | 8.51 |
| 3.6 | 96.4 | 2.55E-09 | 8.59 |
| 4 | 96 | 2.28E-09 | 8.64 |
| 4.5 | 95.5 | 2.02E-09 | 8.70 |
| 5 | 95 | 1.81E-09 | 8.74 |
| 5.5 | 94.5 | 1.63E-09 | 8.79 |
| 6 | 94 | 1.49E-09 | 8.83 |

The trialkylamine/trialkylammonium hydrohalide admixture is reacted with epihalohydrin. At least about a stoichiometric amount of epihalohydrin is reacted with the admixture so that the amine is completely reacted with the epihalohydrin to form the desired product. Preferably, the epihalohydrin to amine plus hydrohalide ratio is from about 1 to about 12, more preferably from about 1.05 to about 1.20 and most preferably from about 1.10 to about 1.20. Amounts in excess of that reacted with the other reagents usually form dihalopropanol under reaction conditions.

Advantageously, epihalohydrin is added to the aqueous amine, amine hydrohalide admixture (hereinafter, reaction mixture). Alternatively the epihalohydrin is added simultaneously with the aqueous admixture to form the desired product. When the epihalohydrin is added, the temperature is advantageously sufficient to result in a desired reaction rate, conveniently to have the reaction proceed with minimal build-up of reactants and a slow exotherm, but slow enough to avoid appreciable diquaternary compound and dihaloalcohol by-product formation. By appreciable is meant less than 1 weight percent diquaternary compound based upon the weight of the desired product, in the case of trimethylamine reacted with epichlorohydrin, 3-chloro-2-hydroxypropyltrimethylammonium chloride, plus diquaternary compound and less than 10 weight percent dihaloalcohol by-product based upon the weight of the desired product plus dihaloalcohol. The temperature of addition is preferably from about 0° C. to about 15° C., more preferably from about 5° C. to about 15° C., most preferably from about 10° C. to about 15° C.

The pH of the reaction mixture will be increased by addition of the epihalohydrin and its reaction with the amine/hydrohalide admixture. Observed pH is preferably from about 7.5 to about 11 after all epihalohydrin is added.

The epihalohydrin is preferably added to the admixture over a period of time rather than all at once to avoid an exotherm which is difficult to control and leads to high levels of aqueous and organic by-products. Conveniently, it is added over a period of from about 1 to about 4 hours.

Alternatively, the process is continuous and comprises adding the epihalohydrin and amine/amine salt admixture in stoichiometric amounts or the preferred ratios in a continuous fashion. The continuous process advantageously has a short residence time in a mixer with a longer residence time in a reactor. A batch process advantageously has the epihalohydrin added slowly to the amine salt admixture with continual mixing during and after the addition.

It has now been found that when using an amine/amine hydrohalide reactant admixture, while a relatively low temperature is advantageous for addition or admixing of epihalohydrin with the amine admixture, a relatively higher temperature is advantageous for at least part of the reaction time. Thus, it is advantageous to have a first time period which preferably includes addition of at least a majority of the epihalohydrin at a temperature at least about 10 degrees centigrade below that of a second period during which the reaction is allowed to proceed further. The second period at a higher temperature advantageously results in a lower residual, unreacted amine in the reaction mixture after reaction is ended. Variations within these two periods are within practice of the invention. For instance, while it is preferable to add the epihalohydrin during the first period while the temperature is lower, optionally at least a portion, preferably less than half, most preferably little to none of the epihalohydrin is added during the second period at the higher temperature.

In a preferred embodiment, the first period extends beyond the time required for addition of the epihalohydrin to allow reaction to include that which is achieved during addition as well as continuing reaction. Time after addition of epihalohydrin is complete during which additional reaction takes place is referred to herein as digest time. The first period preferably includes in addition to an addition time, a digest time, which digest time is preferably sufficient to allow a predetermined amount, preferably at least about 85 percent of the amine and amine salt to react with the epihalohydrin, more preferably is at least about 0.5 hour, most preferably at least about 1 hour. Preferably the digest period ends when sufficient product forms that the rate of formation of dihaloalcohol becomes at least about equal to the rate of formation of product.

While the first period, whether or not it includes a digest time, is preferably at the temperatures stated for addition of epihalohydrin, the second period is at a second, higher temperature sufficiently higher to result in less residual amine after reaction than would be observed if the same reaction (same reactants, total time, addition time, and reaction conditions) except for the temperature of the second period were to take place entirely at the temperature used during the first period. This second temperature is preferably at least about 10 degrees centigrade above that used for the first period, and is preferably less than 50° C. but at least 15° C., more preferably less than 50° C. but at least 30° C., most preferably less than 50° C. but at least 40° C. The second period preferably is a digest time, which digest time is preferably sufficient to result in less residual amine, more preferably is at least about 0.5 hour, most preferably at least about 2 hours. Preferably, this digest time ends when at least about 90 weight percent of the amine, more preferably at least about 99 weight percent of the amine has reacted, most preferably when less than about 50 ppm of amine remains. Preferably the second period ranges from about 0.5 to about 4 hours, most preferably the digest is from about 1 to about 3 hours.

Those skilled in the art will recognize that the present invention includes variations such as gradual increase in temperature from one period to another, for instance in response to the reaction exotherm. Even when there is gradual increase there is a period within a first temperature range and a second period within a second temperature range. In such cases, the preferred period of time at any individual temperature will be shorter than is preferred when there are two relatively constant temperatures. The term "relatively constant" is used to recognize that in practice there is often variation within a temperature held "constant"; for instance, a thermostat may allow a few degrees above and below a set temperature. Such a temperature held within a range is more constant than a continually rising or falling temperature. In reactions where there is changing temperature, the temperature during a period is taken as the average temperature during the period. The invention also includes use of more than two or three temperatures, for instance several short digests at different temperatures.

After reaction of epihalohydrin and trialkylamine and its salt has reached a predetermined stage of completion, preferably is essentially complete, that is at least about 90 percent by weight, more preferably 99 percent by weight of the limiting reactant (preferably the amine plus trialkylamine salt) is reacted, the reaction is ended by removal of the epihalohydrin by any means within the skill in the art such as by organic solvent extraction or vacuum azeotropic distillation.

Some by-products are unavoidably produced and are optionally reacted suitably before, after, or when possible during the process of the invention. Epoxy by-product, in the case of reacting epichlorohydrin with trimethylamine, 2,3-epoxypropyltrimethylammonium chloride, is optionally converted to 3-chloro-2-hydroxypropyltrimethylammonium chloride product by hydrochlorination. Hydrochlorination is within the skill in the art, for instance, where an equimolar amount of hydrochloric acid is added and reacted at 20°–100° C.

After the epichlorohydrin, amine/amine salt reaction is ended, the dihaloalcohol, in the case of epichlorohydrin reacting with trimethylamine, 1,3-dichloro-2-propanol, and residual epichlorohydrin are advantageously separated from the product. Removal is suitably by any method within the skill in the art, but preferably by distillation, preferably azeotropic distillation, most preferably vacuum azeotropic distillation. These means of distillation are preferred because they provide economical separation and do not introduce foreign solvent material. Additionally, vacuum conditions minimize temperatures and resultant thermal degradation of product.

The azeotropic distillation preferably takes place in the presence of sufficient water to provide the azeotropic composition of water with the dihalopropanol, which is 75 weight percent water. The water phase can be allowed to separate and reflux. Initially, there is advantageously enough water to allow loss due to solubility of water removed with the dihalopropanol (including dissolved water) and enough to provide water for the azeotrope. Because of the heterogeneous nature of the azeotrope which allows the water to reflux back, very little additional water will be needed.

Vacuum distillation can be accomplished at any pressure below atmospheric, conveniently from about 50 to about 100 mm Hg (about 7 to about 13 kPa) corresponding to temperatures within the column varying from 30° to 90° C.

Preferably, the product is produced "substantially without" diquaternary or diol by-products. By substantially without it is meant that such by-products are each present in amounts less than 1 weight percent relative to the product halohydroxypropylammonium salt. Preferably there is less than 500 ppm diol by-product in an aqueous solution of 65 weight percent product. More preferably, there is less than 1 percent diquaternary by-product in an aqueous solution of 65 weight percent product. It is believed that intermediates which would otherwise lead to diquaternary by-products are converted to halohydroxypropyltrialkylammonium halide, thus improving efficiency of use of raw materials.

Measuring such concentrations of diquaternary and diol by-products is within the skill in the art, for instance, by liquid chromatography of an aqueous solution of halohydroxypropyltrialkylammonium halide product, which product is most preferably in a concentration of about 65 weight percent in water. Such liquid, preferably paired-ion chromatography is suitably conducted on a system such as the Waters Liquid Chromatograph System commercially available from Millipore, Waters, Chromatography Division. Such a system has a pump, sample injection system, radial column compression system, and a refractive index detector. Suitable columns include, for instance, C-18 reverse-phase columns. A paired-ion chromatography reagent such as that prepared from 3.98 g (grams) of 1-octane sulfonic acid, 116 g sodium perchlorate, 132 g methanol and 1750 g high purity water, filtered through e.g. 0.45 micron paper and degassed 15 minutes under vacuum is suitably used as chromatographic solvent, and a solution such as 5 percent methanol in water (similarly filtered and degassed) is suitably used to flush the column prior to periods of inactivity. These solution concentrations are optionally optimized for some liquid chromatography columns. Determining chromatograph parameters is within the skill in the art, but for the suggested system, suitable combinations include a pump flow rate of 1.5 mL/min. and using a detector having an internal temperature of 40° C. The chromatograph system is preferably used with an integrator, such as that commercially available from Hewlett-Packard and designated as Model 3393. High purity standards are prepared by methods within the skill in the art and used to calibrate the system. The system is preferably purged with the paired-ion chromatography reagent at least until a flat baseline is obtained. Then a weighed sample is introduced into the system, e.g. using a syringe and sample injection valve. Peaks areas are obtained using the system and an integrator and compared with the calibration standard to ascertain concentration. This procedure is within the skill in the art and is taught, for instance, in Dow Analytical Method DOWM 100484 "1,2-Dihydroxypropyl Trimethylammonium Chloride and bis-(Trimethylammonium Chloride)-2-Hydroxypropane in Quat 188 Cationic Monomer".

The level of dihaloalcohol, in the case of epichlorohydrin reacted with trimethylamine hydrochloride, 1,3-dichloro-2-propanol, made is advantageously low, preferably from about 1.0 weight percent in an aqueous solution of about 65 weight percent product to about 10.0 weight percent in an aqueous solution of about 65 weight percent product, more preferably from about 1.0 weight percent in an aqueous solution of about 65 weight percent product to about 5.0 weight percent in an aqueous solution of about 65 weight percent product. Measuring such concentrations of dihaloalcohol by-product is within the skill in the art, for instance, by gas chromatography of an extraction using an organic solvent such as ethyl ether, methylene chloride, perchloroethylene, or carbon tetrachloride of an aqueous solution of halohydroxypropyltrialkylammonium halide product, which product is most preferably in a concentration of about 65 weight percent in water. The organic layer is then analyzed on a gas chromatograph equipped with a column such as a (5 percent phenyl)-methylpolysiloxane column coating commercially available from J&W Scientific under the trade designation DB-5 using a flame ionization detector.

The level of starting trialkylamine hydrochloride left in the reaction solution is advantageously lower than with other processes, preferably less than about 250 ppm in a 65 weight percent solution of the product, more preferably less than about 50 ppm in a 65 weight percent solution of the product. Analysis for residual amine (as exemplified here in the form of the hydrochloride salt) is within the skill in the art. For instance, a sample containing trimethylamine hydrochloride and 3-chloro-2-hydroxypropyltrimethylammonium chloride is conveniently prepared for analysis by preparing a 0.1 weight percent sample in an ion chromatography mobile phase solution. The sample is analyzed on an ion chromatography system using a poly(butadiene)maleic acid absorbed onto amorphous silica column commercially available from Waters Corporation under the trade designation IC-Pak™ Cation M/D column. The analysis is done using a conductivity detector. The mobile phase is a 98 weight percent solution of 3 millimolar (mM) $HNO_3$/0.1 mM EDTA (ethylenediaminetetraacetic acid) and 2 weight percent isopropanol.

The following examples are presented to illustrate the invention and are not to be interpreted as limiting it. All percentages, pans and ratios are by weight unless otherwise stated. Examples (Ex.) of the invention are designated numerically, while Comparative Samples (CS) are not examples of the invention and are designated alphabetically. Unless designated otherwise, compounds are analyzed as described in the preceding paragraphs.

EXAMPLES

Example 1: Preparation of 3-Chloro-2-hydroxypropyl Trimethylammonium Chloride To a 5 neck, 250 mL, jacketed round bottom flask equipped with a stir bar, condenser, thermometer, and pH probe is added 99.61 g of a 57.019 weight percent solution of trimethylamine hydrochloride. The solution is brought to 10° C. by a glycol cooling bath at a temperature of about 8° C. A 3.25 g sample of a 21.64 weight percent aqueous solution of trimethylamine is added and raises the pH from 3.88 to 8.51. A sample, 61.7099 g of epichlorohydrin is then added over a three hour time period while a temperature of 10° C. is maintained by a glycol cooling bath at a temperature of about 5° C. The solution is digested for three additional hours, the first hour the temperature is held at 10° C., and the next two hours it is increased by a glycol heating bath at a temperature of about 42° C. and held at 40° C.

Analyses for residual reactants and formed products is then performed by gas chromatography as described hereinbefore using a column for 1,3-dichloro-2-propanol and epichlorohydrin analysis commercially available from J&W Scientific under the trademark designation DB-5; ion chromatography using a cationic column for trimethylamine hydrochloride analysis commercially available from Waters Corporation under the trade designation IC-PAK™ Cation M/D column; high performance liquid chromatography for 1,3-bis(trimethylammonium chloride)-2-hydroxypropane and 2,3-dihydroxypropyltrimethylammonium chloride analysis using a C-18 reverse-phase column commercially available from Waters Corporation, under the trade designation μBondapak C18 10 μm Cartridge and a titration to measure the 3-chloro-2-hydroxypropyltrimethylammonium chloride content. The alkali consumed in the reaction of the 3-chloro-2-hydroxypropyltrimethylammonium chloride to make the 2,3-epoxypropyltrimethylammonium chloride is determined in the titration. Ten mL of 0.5N sodium hydroxide are added to a one gram sample containing the product to be measured. The solution is allowed to stir for ten minutes before titrating with 0.1N hydrochloric acid to determine how much of the sodium hydroxide was used in the reaction with the 3-chloro-2-hydroxypropyltrimethylammonium chloride. The endpoint may be determined by color change using phenolphthalein. The sample that is being analyzed must be free of any 1,3-dichloro-2-propanol because it will also consume sodium hydroxide thus giving artificially low values for the 3-chloro-2-hydroxypropyltrimethylammonium chloride activity.

Analysis shows:

3-chloro-2-hydroxypropyltrimethylammonium chloride: 63.49 weight percent based on weight of total reaction mixture 2,3-epoxypropyltrimethylammonium chloride: 5.93 weight percent 1,3-bis(trimethylammonium chloride)-2-hydroxypropane: 0.34 weight percent epichlorohydrin: 0.53 weight percent 1,3-dichloro-2-propanol: 3.61 weight percent trimethylamine hydrochloride: less than 30 ppm by weight 2,3-dihydroxypropyltrimethylammonium chloride: less than 100 ppm by weight water (by difference): 26.10 weight percent Examples 2–8 and Comparative Samples A–H:
Preparation of 3-Chloro-2-hydroxypropyl
Trimethylammonium Chloride The procedure of Example 1 is repeated for the Examples and Comparative Samples (not examples of the invention) in Table 1 except for the conditions and results noted in the Table.

TABLE 1

| Example or Sample | Temperature of Epi addition | Base | Equivalents of Epi | hours Epi feed | digest | mole percent amine.HCl | Epi Conversion | Weight Percent Chptmac | Weight Percent Diquat | DCP Equivalent (Weight Percent) | ppm TMA—HCl | Chptmac Yield (TMA Basis) | Relative Chptmac Equiv. Amount | Relative Diquat Amount | Relative DCP Equiv. Amount | Comment |
|---|---|---|---|---|---|---|---|---|---|---|---|---|---|---|---|---|
| C.S. A | 10 | none | 1.1 | 3 | 10° C./3 hr. | 100 | 54.98 | 34.42 | 0.00 | 23.64 | 28500 | 49.62 | 59.28 | 0.00 | 40.72 | High TMA—HCl |
| C.S. B | 10 | NaOH | 1.1 | 3 | 10° C./3 hr. | NA | 92.40 | 68.26 | 0.16 | 4.94 | NA | 99.39 | 93.05 | 0.22 | 6.73 | NaOH as Base |
| Ex. 1 | 10 | TMA | 1.1 | 3 | 10° C./1 hr. 40° C./2 hr. | 98.0 | 98.59 | 69.71 | 0.34 | 4.28 | 29 | 100.60 | 93.78 | 0.46 | 5.76 | Good Yield |
| Ex. 2 | 10 | TMA | 1.05 | 3 | 10° C./1 hr. 30° C./2 hr. | 98.0 | 98.02 | 70.26 | 0.36 | 2.50 | 1257 | 100.03 | 96.09 | 0.49 | 3.42 | High TMA—HCl |
| Ex. 3 | 10 | TMA | 1.1 | 3 | 10° C./1 hr. 30° C./2 hr. | 98.4 | 95.93 | 69.23 | 0.13 | 4.54 | 227 | 98.25 | 93.68 | 0.18 | 6.14 | High TMA—HCl |
| Ex. 4 | 10 | TMA | 1.1 | 2 | 10° C./1 hr. 40° C./2 hr. | 97.1 | 98.15 | 68.59 | 0.27 | 4.53 | 15 | 99.23 | 93.46 | 0.37 | 6.17 | Good Yield |
| C.S. C | 10 | TMA | 1.1 | 2 | 10° C./3 hr. | 97.5 | 92.82 | 67.80 | 0.23 | 4.73 | 326 | 97.92 | 93.18 | 0.32 | 6.50 | High TMA—HCl |
| Ex. 5 | 10 | TMA | 1.1 | 2 | 10° C./1 hr. 30° C./3 hr. | 97.4 | 97.78 | 69.49 | 0.25 | 3.83 | 264 | 100.59 | 94.45 | 0.34 | 5.21 | High TMA—HCl |
| Ex. 6 | 10 | TMA | 1.05 | 2 | 10° C./1 hr. 40° C./2 hr. | 97.4 | 99.75 | 69.65 | 0.67 | 2.60 | 1166 | 99.12 | 95.52 | 0.92 | 3.57 | High TMA—HCl |
| C.S. D | 20 | TMA | 1.1 | 3 | 20° C./3 hr. | 97.7 | 93.88 | 67.55 | 1.34 | 5.01 | 281 | 98.17 | 91.41 | 1.81 | 6.78 | High Diquat |
| C.S. E | 30 | NaOH | 1.1 | 3 | 30° C./3 hr. | NA | 96.78 | 65.43 | 2.21 | 6.05 | NA | 95.21 | 88.79 | 3.00 | 8.21 | High Diquat |
| C.S. F | 10 | TMA | 1.1 | 3 | 7.70 | 99.6 | 99.68 | 58.11 | 6.64 | 9.09 | 750 | 83.35 | 78.70 | 8.99 | 12.31 | High Diquat |
| Ex. 7 | 10 | TMA | 1.1 | 3 | 10° C./1 hr. 40° C./2 hr. | 94.7 | 98.44 | 67.88 | 0.23 | 4.89 | 11 | 99.07 | 92.99 | 0.32 | 6.70 | Good Yield |
| Ex. 8 | 10 | TMA | 1.1 | 3 | 10° C./1 hr. 40° C./2 hr. | 92.3 | 97.44 | 66.06 | 0.53 | 5.76 | 7 | 97.21 | 91.31 | 0.73 | 7.96 | Good Yield |
| C.S. G | 10 | TMA | 1.1 | 3 | 10° C./1 hr. 50° C./2 hr | 98.0 | 99.63 | 60.10 | 4.89 | 8.11 | NA | 86.73 | 82.22 | 6.69 | 11.09 | High Diquat |
| C.S. H | 10 | TMA | 1.1 | 3 | 10° C./1 hr. 40° C./2 hr | 89.9 | 96.65 | 63.81 | 0.79 | 6.81 | 14 | 94.66 | 89.36 | 1.11 | 9.54 | High DCP |

Chptmac is 3-chloro-2-hydroxypropyltrimethylammonium chloride
TMA is trimethylamine
Epi is epichlorohydrin
DCP is 1,3-dichloro-2-propanol
Diquat is 1,3-bis(trimethylammonium chloride)-2-hydroxypropane
TMA—HCl is trimethylamine hydrochloride
DCP equivalent is weight % DCP plus equivalent weight % unreacted epichlorohydrin

TABLE 1-continued

| Example or Sample | Temperature of Epi addition | Base | Equivalents of Epi | hours Epi feed | digest | Starting pH | mole percent amine.HCl | Epi Conversion | Weight Percent Chptmac | Weight Percent Diquat | DCP Equivalent (Weight Percent) | ppm TMA—HCl | Chptmac Yield (TMA Basis) | Relative Chptmac Equiv. Amount | Relative Diquat Amount | Relative DCP Equiv. Amount | Comment |
|---|---|---|---|---|---|---|---|---|---|---|---|---|---|---|---|---|---|

Chptmac equivalent is weight % Chptmac plus equivalent weight % Epoxide
NA is not analyzed.
2,3-dihydroxypropyltrimethylammonium chloride amounts are all <500 ppm
Epoxide is 2,3-epoxypropyltrimethylammonium chloride
% is percent
Relative Chptmac Equiv. Amount is Equiv. weight % Chptmac/(Equiv. weight % Chptmac + weight % Diquat + Equiv. weight % DCP)
Relative Diquat Amount is weight % Diquat/(Equiv. weight % Chptmac + weight % Diquat + Equiv. weight % DCP)
Relative DCP Equiv. Amount is Equiv. weight % DCP/(Equiv. weight % Chptmac + weight % Diquat + Equiv. weight % DCP)
Chptmac Yield is moles of Chptmac made/(moles of amine + amine hydrochloride added to reactor)
NaOH is sodium hydroxide The data in Table 1 shows that the use of amounts of free amine within the practice of the invention results in less residual TMA,HCl than in Comparative Sample A where amine hydrochloride is used without free amine. In each example of this invention less than 500 ppm 2,3-dihydroxypropyltrimethylammonium chloride (diol by-product) is observed.

It is also noted when comparing Comparative Sample A with examples of the invention that the Epi conversion is less than 55 percent indicating that the reaction was not proceeding in C. S A. Comparative Sample B illustrates the use of sodium hydroxide as an initial pH adjuster, but does not involve at least two temperatures. Comparative Sample C shows the inability to obtain less than 50 ppm trimethylamine hydrochloride when the initial pH is adjusted and the first period of time has a temperature of 10° C., but the second period of time is a temperature that is also 10° C. Comparative Sample D shows increased amounts of Diquat and DCP when the initial pH is adjusted, but the temperature of the first period is 20° C. Comparative Sample E shows the decreased purity of the product when the pH is initially adjusted, but the reaction temperature is not cold enough to inhibit the higher levels of Diquat and DCP that are made compared to the examples in the invention. Comparitive Sample F shows a higher level of impurities formed when the initial mole percent amine HCl is higher than in the practice of the invention. The Diquat, DCP, and TMA.HCl levels are significantly higher than in examples of the invention. Comparitive Sample G shows an increase in Diquat and DCP formation when the second digest temperature is above the limits in the invention. A strong exotherm was observed when the second digest temperature of 50° C. is reached. It is believed that this exotherm is the cause of the higher Diquat and DCP levels found in this comparitive sample. Comparitive Sample H shows increased levels of Diquat and DCP when the initial mole percent amine HCl is lower than in examples of the invention.

The data in Table 1 also shows that within the practice of the invention, adding a 1.10 mole excess of epichlorohydrin to a pH adjusted mixture of trimethylamine and trimethylamine hydrochloride at 10° C. and allowing a one hour digest at 10° C. and a subsequent two hour digest at 40° C. gives a product with high purity, low residual amine, low Diquat formation, and low Diol formation. Reactions at 20° C. and 30° C. give higher DCP equivalent values and higher Diquat levels resulting in a lower purity product. Reactions with a 1.05 mole excess of epichlorohydrin to trimethylamine and trimethylamine hydrochloride give a product with lower DCP values than with a 1.10 mole excess of epichlorohydrin, low Diquat, but a high level of residual trimethylamine hydrochloride (greater than 500 ppm). The examples that have digest temperatures of 20 or 30° C. give higher residual trimethylamine hydrochloride amounts than the runs that have digest temperatures of 40° C.

We claim:

1. A process for producing halohydroxypropyltrialkylammonium salts by reacting, in a reaction mixture, a trialkylamine hydrohalide salt and the corresponding free amine with an epihalohydrin, wherein the free trialkylamine is present in an amount corresponding to from about 1 to about 10 mole percent of the combination of free amine and amine hydrohalide and wherein the epihalohydrin is admixed and allowed to react for a first period of time with the free amine and hydrohalide salt at a first temperature less than a second temperature at which the epihalohydrin is allowed to further react with the amine and hydrohalide salt for a second period of time wherein the second temperature is sufficiently greater than the first that less unreacted amine is present after reaction than is present if the same reactants are admixed and reacted at the first temperature for a time equal to the sum of the first and second periods of time.

2. The process of claim 1 wherein the epichlorohydrin is admixed and allowed to react with the free amine and amine hydrohalide at a first temperature of from about 0° C. to about 15° C. for the first period of time and the admixture is allowed to react further at a second temperature less than 50° C. but at least 15° C. for the second period of time.

3. The process of claim 2 wherein the first period comprises a first addition time for epihalohydrin addition and a second time which is a digest time.

4. The process of claim 3 wherein the first period comprises a first time of from about 1 to about 4 hours and a digest time of from 0.5 to about 2 hours.

5. The process of claim 3 wherein the second period is from about 0.5 to about 4 hours.

6. The process of claim 2 wherein there is from about 90 to about 99 mole percent amine hydrohalide.

7. The process of claim 6 wherein the first temperature is from about 0° C. to about 15° C. and the second temperature is less than 50° C. but at least 15° C.

8. The process of claim 7 wherein the reaction mixture comprises water, epichlorohydrin, and trialkylamine, and trialkylamine hydrochloride wherein the alkyl group has from 1 to about 20 carbon atoms.

9. The process of claim 7 wherein the trialkylamine is trimethylamine, dimethyl stearyl amine or dimethyl dodecylamine.

10. The process of claim 7 wherein the reaction mixture comprises water, epichlorohydrin, and trimethylamine, and trimethylamine hydrochloride.

* * * * *